United States Patent [19]

Verbicky, Jr. et al.

[11] Patent Number: 4,577,033

[45] Date of Patent: Mar. 18, 1986

[54] HETEROCYCLIC QUATERNARY AMMONIUM SALTS AS PHASE TRANSFER CATALYSTS FOR AROMATIC ETHER IMIDE PREPARATION

[75] Inventors: John W. Verbicky, Jr., Scotia; Alice M. Colley, Latham, both of N.Y.

[73] Assignee: General Electric Company, Schenectady, N.Y.

[21] Appl. No.: 691,037

[22] Filed: Jan. 14, 1985

[51] Int. Cl.$^4$ .............................................. C07D 209/48
[52] U.S. Cl. .................................... 548/461; 260/692; 546/98; 548/451; 548/476; 548/481
[58] Field of Search ............... 548/461, 481, 476, 451; 546/98; 260/692

[56] References Cited

U.S. PATENT DOCUMENTS

| | | | |
|---|---|---|---|
| 2,389,427 | 11/1945 | Gertler | 548/480 |
| 3,246,009 | 4/1966 | Loev | 548/480 |
| 4,273,674 | 6/1981 | Lignon, Jr. et al. | 548/480 |
| 4,273,712 | 6/1981 | Williams | 260/326 |

OTHER PUBLICATIONS

K. Isagawa et al., Chem. Abstracts 81:151587v (1974). Catalysis by Certain Amines in an Aqueous Phase.
H. Dow et al., Chem. Abstracts 90:21867m (1979). Autocatalyzed Dequaternization Reactions in Phase Transfer Catalysis.

*Primary Examiner*—Donald G. Daus
*Assistant Examiner*—Mary E. Ceperley
*Attorney, Agent, or Firm*—William H. Pittman; James C. Davis, Jr.; James Magee, Jr.

[57] ABSTRACT

Heterocyclic quaternary ammonium salts such as N,N-di-n-butylpiperidinium bromide are excellent phase transfer agents for the preparation of aromatic ethers, as by the reaction of the disodium salt of bisphenol A with 4-nitro-N-methylphthalimide.

10 Claims, 1 Drawing Figure

(I) 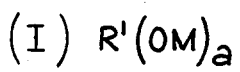
(II) 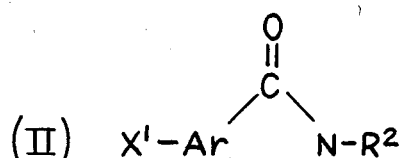
(III) 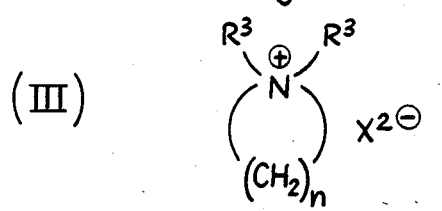
(IV) 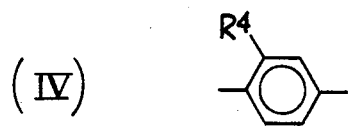
(V) 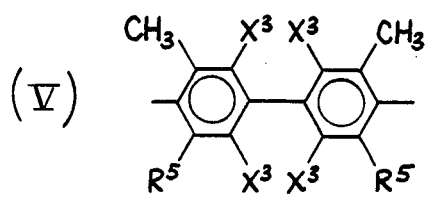
(VI) 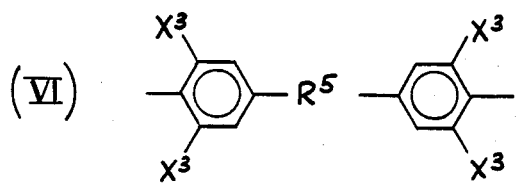

HETEROCYCLIC QUATERNARY AMMONIUM SALTS AS PHASE TRANSFER CATALYSTS FOR AROMATIC ETHER IMIDE PREPARATION

This invention relates to the preparation of aromatic ether imides, and more particularly to improved phase transfer catalysts for use in said preparation.

Aromatic ether imides are a known class of compounds. It is also known that various aromatic ether bisimides such as 2,2-bis[4-(3,4-dicarboxyphenoxy)-phenyl]-propane bis-N-methylimide may be converted to dianhydrides, which in turn may be reacted with diamines to produce polyetherimides. Certain bisimides can also be reacted directly with diamines to produce polyetherimides, as disclosed and claimed in copending, commonly assigned application Ser. No. 505,636, filed June 20, 1983. The analogous monoimides and the corresponding monoanhydrides can be used, for example, as end-capping or chain-stopping agents for polyetherimides.

A convenient method of preparing aromatic ether imides and similar compounds is by the nucleophilic displacement reaction of a substituted aromatic compound, most often an imide such as a substituted phthalimide, wherein the substituents may be, for example, halo or nitro, with an alkali metal salt of a hydroxyaromatic compound. This reaction is often conveniently effected in solution in a substantially non-polar organic solvent, in the presence of a phase transfer catalyst. U.S. Pat. No. 4,273,712 describes suitable reaction conditions and the use of various quaternary ammonium and phosphonium salts as phase transfer catalysts; its disclosure is incorporated by reference herein.

It is frequently found that a portion of a quaternary ammonium phase transfer catalyst is converted to nitrosamine by-products during the displacement reaction. Said by-products are, for the most part, insoluble in water and remain in the ether imide product even after washing with water and/or aqueous base. It is of interest, therefore, to develop phase transfer catalysts which generate either no nitrosamines or water-soluble nitrosamines which can be easily removed during the aqueous wash steps.

A principal object of the present invention, therefore, is to provide an improved method for the preparation of aromatic ether imides by the reaction of substituted aromatic imides with alkali metal phenoxides.

A further object is to provide improved phase transfer catalysts for use in said reaction.

Still another object is to provide phase transfer catalysts which generate either no nitrosamine by-products or nitrosamines which are easily removed from the product.

Other objects will in part be obvious and will in part appear hereinafter.

In one of its aspects, the present invention comprises an improvement in a method for preparing an aromatic ether by the reaction, in a non-polar organic solvent in the presence of a phase transfer catalyst, of (A) at least one hydroxyaromatic compound alkali metal salt having formula I in the drawings, where $R^1$ is an aromatic radical containing about 6–30 carbon atoms, M is an alkali metal and a is 1 or 2, with (B) at least one activated halo- or nitro-substituted aromatic compound; said improvement comprising using as said phase transfer catalyst (C) at least one heterocyclic quaternary salt having formula III, wherein $R^3$ is a lower alkyl radical, $X^2$ is an anion forming atom or radical and n is an interger from 4 to 6.

Reagent A in the method of this invention is at least one alkali metal salt of a mono- or dihydroxyaromatic compound, depending on whether a is 1 or 2. The M value may by any alkali metal; it is usually lithium, sodium or potassium and preferably sodium.

The $R^1$ value may be any aromatic radical containing about 6–30 carbon atoms. It may be hydrocarbon radical or may contain other atoms such as oxygen or sulfur. Illustrative monovalent radicals (i.e., those derived from compounds in which a is 1) include phenyl, m-tolyl, p-tolyl, 1-naphthyl, 2-naphthyl, p-chlorophenyl and 4-bromo-1-naphthyl.

Most often, $R^1$ is a divalent aromatic radical; i.e., a is 2. Illustrative radicals of this type are derived from such compounds as resorcinol. hydroquinone, 4,4'-dihydroxybiphenyl, 4,4'-dihydroxy-3,3',5,5'-tetra-methylbiphenyl, 4,4'-dihydroxydiphenylmethane, 3,4'-dihydroxydiphenylmethane, 2,2-bis(2-hydroxyphenyl)propane, 2,2-bis(4-hydroxyphenyl)propane (hereinafter "bisphenol A"), 2-(3-hydroxyphenyl)-2-(4-hydroxyphenyl)propane, 1,1-bis(4-hydroxyphenyl)ethane, 2,2-bis(4-hydroxyphenyl)pentane, 4,4'-dihydroxybenzophenone, bis(4-hydroxyphenyl) ether, bis(4-hydroxyphenyl)sulfide, bis(4-hydroxyphenyl) sulfoxide, bis(4-hydroxyphenyl) sulfone and 3-hydroxyphenyl 4-hydroxyphenyl sulfone.

The preferred $R^1$ radicals are those having formula IV–VI, wherein each $R^4$ is independently hydrogen or methyl, $R^5$ is a straight-chain or branched alkylene radical containing 1–5 carbon atoms and is most often the isopropylidene radical, and each $X^3$ is independently hydrogen or halogen (usually chlorine or bromine). Mixtures of the foregoing formulas are also contemplated. Especially desirable is the radical derived from bisphenol A by the removal of both hydroxy groups therefrom, and having formula VI wherin $R^5$ is isopropylidene and each $X^3$ is hydrogen.

Reagent B us at least one activated halo- (usually fluoro- or chloro-) or (preferably) nitro-substituted aromatic compound. By "activated" in the context of this invention is meant a compound having an electron-deficient aromatic ring. Electron deficiency may be achieved by the presence of electron-withdrawing substituents such as halo, nitro, keto, cyano, carboxy, carbalkoxy, perfluoroalkyl or the like, or by the presence of hetero atoms such as nitrogen (e.g., as part of a pyridine ring).

Most often, reagent B is at least one substituted imide having formula II, wherein Ar is an aromatic radical, $R^2$ is hydrogen or a hydrocarbon-based radical containing about 1–13 carbon atoms and $X^1$ is halo or nitro. The Ar value may be any aromatic radical which contains about 6–30 carbon atoms and which is capable of forming an imide. In general, these are radicals derived from o-dicarboxylic acids such as phthalic acid and 2,3-naphthalendicarboxylic acid; however, radicals derived from acids such as 1,8-naphthalenedicarboxylic acid are also suitable. Most preferably, Ar is derived from phthalic acid; i.e., it is the o-phenylene radical.

The $R^2$ value is hydrogen or a hydrocarbon-based radical containing from 1 to about 13 carbon atoms. The term "hydrocarbon-base radical" as used herein includes hydrocarbon radicals and radicals containing substituents and/or hetero atoms which do not, in the context of this invention, substantially alter their hydrocarbon character. A preferred subgenus of $R^2$ radicals consist of alkyl and especially lower alkyl radicals; i.e., alkyl radicals containing up to 7 carbon atoms. The preferred lower alkyl radical is methyl.

A second preferred subgenus consists of electron-deficient radicals. For the most part, these comprise aromatic hydrocarbon radicals containing one or more strongly electron-withdrawing substituents and heterocyclic radicals having aromatic character. Compounds in which $R^2$ is of this type are disclosed and claimed in the aforementioned application Ser. No. 505,636, the disclosure of which is incorporated by reference herein.

Suitable aromatic hydrocarbon radicals include phenyl, naphthyl and the like containing such substituents as halo, nitro, keto, carbalkoxy, cyano and perfluoroalkyl. At least one of said electron-withdrawing substituents is preferably ortho or para to the free valence bond (i.e., the one attached to the imide nitrogen atom). The trifluoromethylphenyl radicals are particularly preferred.

Suitable heterocyclic radicals having aromatic character include those with 5- or 6-membered rings and aromatic unsaturation of the type existing in pyrrole and pyridine. These radicals preferably contain 1-3 and especially 1 or 2 hetero atoms of which at least one is nitrogen and the others, if present, are nitrogen or sulfur. They are usually unsubstituted but may be substituted, especially with electron-withdrawing substituents such as those previously enumerated. The free valence bond is preferably in the 2- or 4-position with respect to a hetero atom. If the ring contains more than one hetero atom, and especially if it is 5-membered, the free valence bond is preferably attached to the single carbon atom between two of said hetero atoms.

Illustrative 5-membered heterocyclic radicals are pyrrolyl, 2-thiazolyl, 2-imidazolyl and 2-(1,3,4-thiadiazolyl). Illustrative 6-membered radicals are, 2-pyridyl, 4-pyridyl, 2-pyrimidyl, 2-pyrazyl, 2-(1,4-thiazolyl and 2-(1,3-thiazoyl). Particularly preferred heterocyclic radicals are the pyridyl radicals, especially 2-pyridyl and 4-pyridyl.

Reagent C, the phase transfer catalyst, is at least one heterocyclic quaternary salt having formula III. In that formula, $R^3$ is a lower alkyl radical; it is preferably a straight chain radical and more preferably contains 1-4 carbon atoms.

The $X^2$ value may be any anion which is stable under the conditions of the invention; suitable anions include chloride, bromide, sulfate, p-toluenesulfonate and methanesulfonate. Because of the ready availability and particular suitability of bromide reagents for the preparation of reagent C as described hereinafter, $X^2$ is usually bromide.

The interger n may be 4, 5 or 6, whereupon reagent C is a pyrrolidinium, piperidinium or azacycloheptylammonium salt, respectively. Most often, n is 5.

Illustrative heterocyclic quaternary salts which may be used as reagent C are N,N-di-n-butylpiperidinium bromide, which is preferred, and N,N-dimethylpyrrolidinium bromide. Such salts may be prepared by known methods, typically by the reaction of a suitable heterocyclic amine with a carbonium ino-generating compound such as an alkyl bromide, chloride, methanesulfonate or the like.

According to the present invention, the reaction between reagents A and B is ordinarily effected at a temperature within the range of about 25°-150° C., preferably about 100°-120° C., in a non-polar organic solvent such as benzene, toluene, xylene, chlorobenzene, o-dichlorobenzene, tetrahydrofuran, acetonitrile, octane or the like. It is preferred to use approximately equivalent amounts of the two reagents, which includes the use of a slight excess (usually no more than about 5 mole percent) of either.

Reagent C is usually present in the reaction mixture in the amount of about 0.005-0.25 equivalent per equivalent of reagent A. For the purposes of this invention, the equivalent weight of reagent A is its molecular weight divided by the number of aromatic hydroxy groups present therein, and that of reagent C is equal to its molecular weight.

Also contemplated as part of the invention are compositions comprising (A) at least one hydroxyaromatic compound alkali metal salt, (B) at least one substituted aromatic compound and (C) at least one heterocyclic quaternary salt, all as previously defined herein, preferably in the above-described proportions. Said compositions are useful for conversion to aromatic ether imides by the previously described reaction.

The method of this invention is illustrated by an example in which N,N-di-n-butylpiperidinium bromide was added as a phase transfer catalyst in various amounts to a mixture of 1.5 grams (0.0055 mole) of bisphenol A disodium salt, 2.27 grams (0.011 mole) of 4-nitro-N-methylphthalimide, 5.7 grams of toluene and 0.31 gram of o-terphenyl (used as an internal standard). The mixtures were heated to reflux and sampled after two hours, with yield of 2,2-bis[4-(3,4-dicarboxyphenoxy)phenyl]propane bis-N-methylimide being determined by liquid chromatography. The results are listed in the following table.

| Run | Equivs. catalyst per equiv. of bisphenol A salt | Yield of bisimide, % |
|-----|------------------------------------------------|----------------------|
| 1   | 0.0225                                         | 94                   |
| 2   | 0.0175                                         | 94                   |
| 3   | 0.0125                                         | 93                   |

In another run, similar to Run 3 except that the reaction was stopped at a 78% yield of bisimide, the organic liquid phase was analyzed for nitrosamines and 3.5 ppm. of di-n-butylnitrosamine was found. A control run using the same proportion of tetra-n-butylammonium bromide as a phase transfer catalyst produced 11 ppm. of the same nitrosamine.

What is claimed is:

1. In a method for preparing an aromatic ether imide by the reaction, in a non-polar organic solvent in the presence of a phase transfer catalyst, of (A) at least one hydroxyaromatic compound alkali metal salt having formula I

where $R^1$ is an aromatic radical containing about 6-30 carbon atoms, M is an alkali metal and a is 1 or 2, with (B) at least one substituted imide having formula II

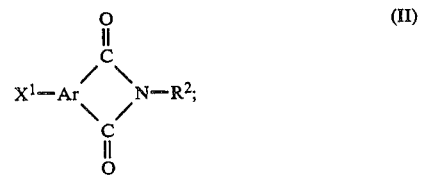

wherein
Ar is an aromatic radical, $R^2$ is hydrogen or a hydrocarbon-based radical containing about 1-13 carbon atoms and $X^1$ is halo or nitro;

the improvement which comprises using as said phase transfer catalyst (C) at least one heterocyclic quaternary salt having formula III

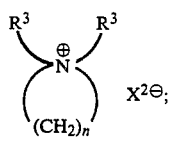 (III)

wherein $R^3$ is a lower alkyl radical, $X^2$ is one equivalent of an anion-forming atom or radical and n is an integer from 4 to 6.

2. A method according to claim 1 wherein the hydroxyaromatic compound is bisphenol A and reagent B is a substituted phthalimide.

3. A method according to claim 2 wherein $R^3$ is a straight chain radical and $X^2$ is bromide.

4. A method according to claim 3 wherein reagent C is present in the amount of about 0.005-0.25 equivalent per equivalent of reagent A.

5. A method according to claim 4 wherein M is sodium and $X^1$ is nitro.

6. A method according to claim 5 wherein $R^2$ is a lower alkyl radical.

7. A method according to claim 6 wherein $R^2$ is methyl.

8. A method according to claim 7 wherein reagent C is N,N-di-n-butylpiperidinium bromide.

9. A method according to claim 5 wherein $R^2$ is an electron-deficient radical.

10. A method according to claim 9 wherein reagent C is N,N-di-n-butylpiperidinium bromide.

* * * * *